US007375225B2

(12) United States Patent
Taniguchi et al.

(10) Patent No.: US 7,375,225 B2
(45) Date of Patent: *May 20, 2008

(54) 4-CYANOCOUMARIN DERIVATIVES AND USES THEREOF

(75) Inventors: Yoshio Taniguchi, Nagano (JP); Toshiki Koyama, Nagano (JP); Chihaya Adachi, Hokkaido (JP); Tomoyasu Saitou, Tokyo (JP); Makoto Satsuki, Okayama (JP); Akira Shinpo, Okayama (JP); Sadaharu Suga, Okayama (JP); Shizuo Tokito, Tokyo (JP); Hisayoshi Fujikawa, Aichi (JP); Koji Noda, Aichi (JP); Atsushi Miura, Aichi (JP); Yasunori Taga, Aichi (JP)

(73) Assignee: Kabushiki Kaisha Hayashibara Seibutsu Kagaku Kenkyujo, Okayama-shi (JP)

( * ) Notice: Subject to any disclaimer, the term of this patent is extended or adjusted under 35 U.S.C. 154(b) by 700 days.

This patent is subject to a terminal disclaimer.

(21) Appl. No.: 10/347,335

(22) Filed: Jan. 21, 2003

(65) Prior Publication Data
US 2003/0176520 A1 Sep. 18, 2003

Related U.S. Application Data

(60) Division of application No. 09/982,772, filed on Oct. 22, 2001, now Pat. No. 6,573,380, which is a continuation-in-part of application No. 09/521,857, filed on Mar. 9, 2000, now abandoned.

(51) Int. Cl.
C07D 221/22 (2006.01)
(52) U.S. Cl. ........................................... 546/71
(58) Field of Classification Search ............. 546/63, 546/71
See application file for complete search history.

(56) References Cited

U.S. PATENT DOCUMENTS 4,769,292 A 9/1988 Tang et al.
6,573,380 B2 * 6/2003 Taniguchi et al. ............. 546/71

FOREIGN PATENT DOCUMENTS

| DE | 3236241 | | 4/1984 |
|---|---|---|---|
| DE | 3322946 | * | 1/1985 |
| DE | 3609804 | | 9/1987 |
| EP | 0025136 | | 3/1981 |
| EP | 0101897 | | 3/1984 |
| EP | 0435262 | | 7/1991 |
| EP | 0797376 | | 9/1997 |
| JP | 54-151024 | | 11/1979 |
| JP | 58-29803 | | 2/1983 |
| JP | 59-56403 | | 3/1984 |
| JP | 63-23901 | | 2/1988 |
| JP | 10-204085 | * | 8/1988 |
| JP | 64-33104 | | 2/1989 |
| JP | 6-9892 | | 1/1994 |
| JP | 6-329654 | | 11/1994 |
| JP | 10-60427 | | 3/1998 |
| JP | 10-204085 | * | 8/1998 |

OTHER PUBLICATIONS

Suzuki, R et al 'Coumarin compound, photosensitizer containing it, and visible light-curable photosensitive compostion, ink, an material containing it' (1998) CA 129:209331.*
Shikizai-Kyokai-Shi, vol. 70, No. 2, pp. 102-111 (1997).
Patent Abstracts of Japan, Publication No. 04015201, Publication Date Jan. 20, 1992.
Patent Abstracts of Japan, Publication No. 08337582, Publication Date Dec. 24, 1996.
Patent Abstracts of Japan, Publication No. 09291087, Publication Date Nov. 11, 1997.
Patent Abstracts of Japan, Publication No. 09328482, Publication Date Dec. 12, 1997.
Patent Abstracts of Japan, Publication No. 09227547, Publication Date Sep. 2, 1997.
Patent Abstracts of Japan, Publication No. 09208574, Publication Date Aug. 12, 1997.
Patent Abstracts of Japan, Publication No. 10204085, Publication Date Aug. 4, 1998.
Patent Abstracts of Japan, Publication No. 07267942, Publication Date Oct. 17, 1995.
Patent Abstracts of Japan, Publication No. 06009952, Publication Date Jan. 18, 1994.
Patent Abstracts of Japan, Publication No. 06332172, Publication Date Feb. 12, 1994.
Patent Abstracts of Japan, Publication No. 09221486, Publication Date Aug. 26, 1997.
Patent Abstracts of Japan, Publication No. 09268185, Publication Date Oct. 14, 1997.
Patent Abstracts of Japan, Publication No. 10017562, publication Date Jan. 20, 1998.
Drexhage, et al., "Laser dyes" 102:133552 1985.
Hahn, et al. "Cyano(thiazolyl)courmarin fluorescent dyes" 108:7509 1988.
Suzuki, et al. "Coumarin compound, photosensitizer containing it, and visible light-curable photosensitive composition, ink, and material containing it" 129:209331 1998.

* cited by examiner

*Primary Examiner*—Celia Chang
(74) *Attorney, Agent, or Firm*—Browdy and Neimark

(57) ABSTRACT

4-Cyanocoumarin derivatives which have a distinct sensitivity to visible light, distinct luminescent ability, and satisfactory applicability for photochemical polymerization, dye lasers, and organic electroluminescent elements. Since most of the derivatives have a fluorescent maximum wavelength of 600 to 650 nm, particularly, 610 to 630 nm, they are extremely useful as luminescent agents for organic EL elements which emit visible light in a red-color region, and can be quite useful as luminescent agents in organic EL elements and laser-active substances in dye lasers, as well as luminous bodies as lighting sources for lighting devices, and information displays for visually displaying information.

1 Claim, 3 Drawing Sheets

4-CYANOCOUMARIN DERIVATIVES AND USES THEREOF

CROSS-REFERENCE TO RELATED APPLICATION

This application is a divisional of application Ser. No. 09/982,772, filed Oct. 22, 2001, now U.S. Pat. No. 6,573,380, which is a continuation-in-part (CIP) of U.S. application Ser. No. 09/521,857, filed Mar. 9, 2000, now abandoned, entitled "4-Cyanocoumarin derivatives", the disclosure of which is hereby incorporated herein by reference.

FIELD OF THE INVENTION

The present invention relates to a functional organic compound and uses thereof, more particularly, to a novel 4-cyanocoumarin derivative useful in photochemical polymerization, dye lasers, and electroluminescent elements (abbreviated as "organic EL elements", hereinafter).

DESCRIPTION OF THE PRIOR ART

In a multimedia age, photochemical polymerization has been widely used in many fields without restriction to the field of synthetic resins, and it is now being extensively used in the field of information recordings, including memories (hereinafter referred to as "recordings") and electronic equipments, such as paints, lithographic plates for printing, printing circuits, and integrated circuits. Photochemical polymerization is a technique for polymerizing polymeric compounds by irradiating light and is roughly classified into (i) photopolymerization that initiates the polymerization of polymeric compounds by directly irradiating them for activation, and (ii) photosensitization polymerization that polymerizes polymeric compounds by irradiating them in the presence of photosensitizes to make them into a growth-active form. In both cases, as characteristic features, the initiation and the suspension of polymerization can be controlled by flashing excited light, and the rate and the degree of polymerization can be easily controlled by appropriately selecting the strength and the wavelength of the light. The photochemical polymerization can be proceeded even at a relatively low temperature because it only requires a lesser energy for initiating polymerization.

As a new development of information recordings such as holography and lithographic plates for printing and due to the advantageous features of photochemical polymerization, photopolymeric compositions, which can be polymerized by irradiating visible light such as those of argon ion lasers, helium/neon lasers, and second harmonics of YAG lasers, are now rapidly in great demand. However, polymeric compounds and polymerization initiators, which are generally incorporated into photopolymeric compositions, absorb ultraviolet rays only, and this inevitably needs photosensitizes as a technical factor when polymerizing the compositions with visible light. In photopolymeric compositions used for information recordings and electronic equipments, polymeric compounds should be used in combination with photosensitizes, polymerization initiators, and binding resins, which can be selected from materials to suite their use. In general, there may be employed a technique for selecting materials other than photosensitizes and then selecting photosensitizes capable of sensitizing the selected polymeric compounds and/or polymerization initiators in such a manner of trial and error.

Desired features needed for photosensitizes are as follows: They should have a relatively-high molecular absorption coefficient in a visible region, sensitize polymeric compounds and polymerization initiators, exert a relatively-high sensitization efficiency, have a satisfactory solubility in both solvents and another compounds to be incorporated, and have a satisfactory stability. Representative examples of such photosensitizes are merocyanine dyes as disclosed in Japanese Patent Kokai No. 151,024/79, cyanine dyes as disclosed in Japanese Patent Kokai No. 29,803/83, stilbene derivatives as disclosed in Japanese Patent Kokai No. 56,403/84, coumarin derivatives as disclosed in Japanese Patent Kokai No. 23,901/88, pyran derivatives as disclosed in Japanese Patent Kokai No. 329,654/94, and methylene blue derivatives as disclosed in Japanese Patent Kokai No. 33,104/89. All of these compounds have both merits and demerits, and there found no photopolymeric compound which comprise various materials and constantly exert the aforesaid characteristic features.

Organic compounds which are sensitive to light, more particularly, those which are capable of emitting light are also useful in the field of dye lasers and electroluminescence.

In the field of dye lasers, as disclosed, for example, by Kaoru IGARASHI in "Shikizai-Kyokai-shi", Vol. 70, No. 2, pp. 102-111 (1997), since dye laser's lasing was reported in 1960, compounds, which emit light in a visible region, have been eagerly screened. As the progress of information recording technology, compounds which emit light in a longer wavelength region, and more particularly, in a visible region, have been needed more and more.

In the field of information displays, electroluminescent elements (hereinafter abbreviated as "EL elements") are now highlighted as a display element for the forthcoming generation. At present, cathode-ray tubes are predominantly used in a larger size of information displays such as computer termini and TV receivers. The cathode-ray tubes, however, have a relatively large mass and weight and a relatively high operation voltage, and this hinders their applicability for commonly used equipments and smaller size of portable ones whose transportability is highly valued. More required are the information displays which are relatively small in size like in a thinner and lighter plain form and which operate at a lower operation voltage and wattage. Due to advantageous features of relatively-low operation voltage and wattage, liquid crystal elements are now commonly used in many fields. However, the information displays using such elements will change in contrast when viewed from different angles, display information clearly only within a specific angle, and require blacklight, resulting in a problem of that they could not be reduced their wattage as much as they are expected. As a display element to overcome these drawbacks, there appeared an electroluminescent element, i.e., an organic EL element.

Organic EL elements are generally luminous elements which have a thin film, containing a luminescent agent and being inserted between a cathode and anode, and which utilize luminescence such as fluorescence or phosphorescence emitted by the luminescent agent in such a manner that a direct current voltage is energized between the cathode and anode to supply positive holes and electrons to the film and to couple the positive holes and electrons together to make the agent into an excited state, and the excited agent returns to the ground state while emitting luminescence. As characteristic features, organic EL elements can be appropriately changed its luminous color tint by selecting an appropriate host luminous agent and varying a guest luminescent agent used together with the host. Depending on the combination of luminous agents as the host and guest, the brightness and the life expectancy of luminescence can possibly be improved by a large margin. It is said that organic EL elements are theoretically excellent luminous-elements because of the following merits: Information displays with such organic EL elements are free of view angles because the elements autonomously emit light, and are low in energy consumption because the elements need no backlight.

In respect of organic EL elements which emit light in a green-color region, there is a report for improving luminous efficiency by using a luminescent agent as a guest. However, there found no effective luminescent agent usable as a guest in organic EL elements for light in a red-color region. Therefore, the latter is far from emitting a complete red-color luminescence and has a relatively-short life expectancy and poor durability and reliability. For example, organic EL elements, as disclosed in Japanese Patent Kokai No. 60,427/98 and U.S. Pat. No. 4,769,292, can only emit an insufficient brightness and an incomplete red-color emission. Accordingly, conventional organic EL elements would still be problematic in realizing a full color emission.

To supply organic EL elements at a relatively-lower cost, it is essential to explore a luminescent agent which does not intrinsically require doping of a guest luminescent agent in addition to simplify the total structure of the elements and to facilitate the vapor deposition in their processings. Many proposals have been made on luminescent agents used for organic EL elements, however, there found no compound which fulfills the aforesaid requirements.

SUMMARY OF THE INVENTION

In view of the foregoing, the object of the present invention is to provide a novel organic compound which has a distinct sensitivity to a visible light and a relatively-high luminescent ability, and its uses in photochemical polymerization, organic EL elements, and dye lasers.

To attain the above object, the present inventors eagerly screened compounds and found that a series of 4-cyanocoumarin derivatives, which are obtainable by cyanizing coumarin compounds having a julolidine structure intramolecularly, are highly susceptible to visible light and extremely useful in photochemical polymerization. They also found that the 4-cyanocoumarin derivatives exert a distinct luminescent ability in a visible region and can be advantageously used in dye lasers and organic EL elements. The present invention was made based on the preparation of the novel 4-cyanocoumarin derivatives and the finding of their industrially useful properties.

The present invention solves the above object by providing the novel 4-cyanocoumarin derivatives.

BRIEF EXPLANATION OF THE ACCOMPANYING DRAWINGS

DETAILED DESCRIPTION OF THE INVENTION

Figure 1:
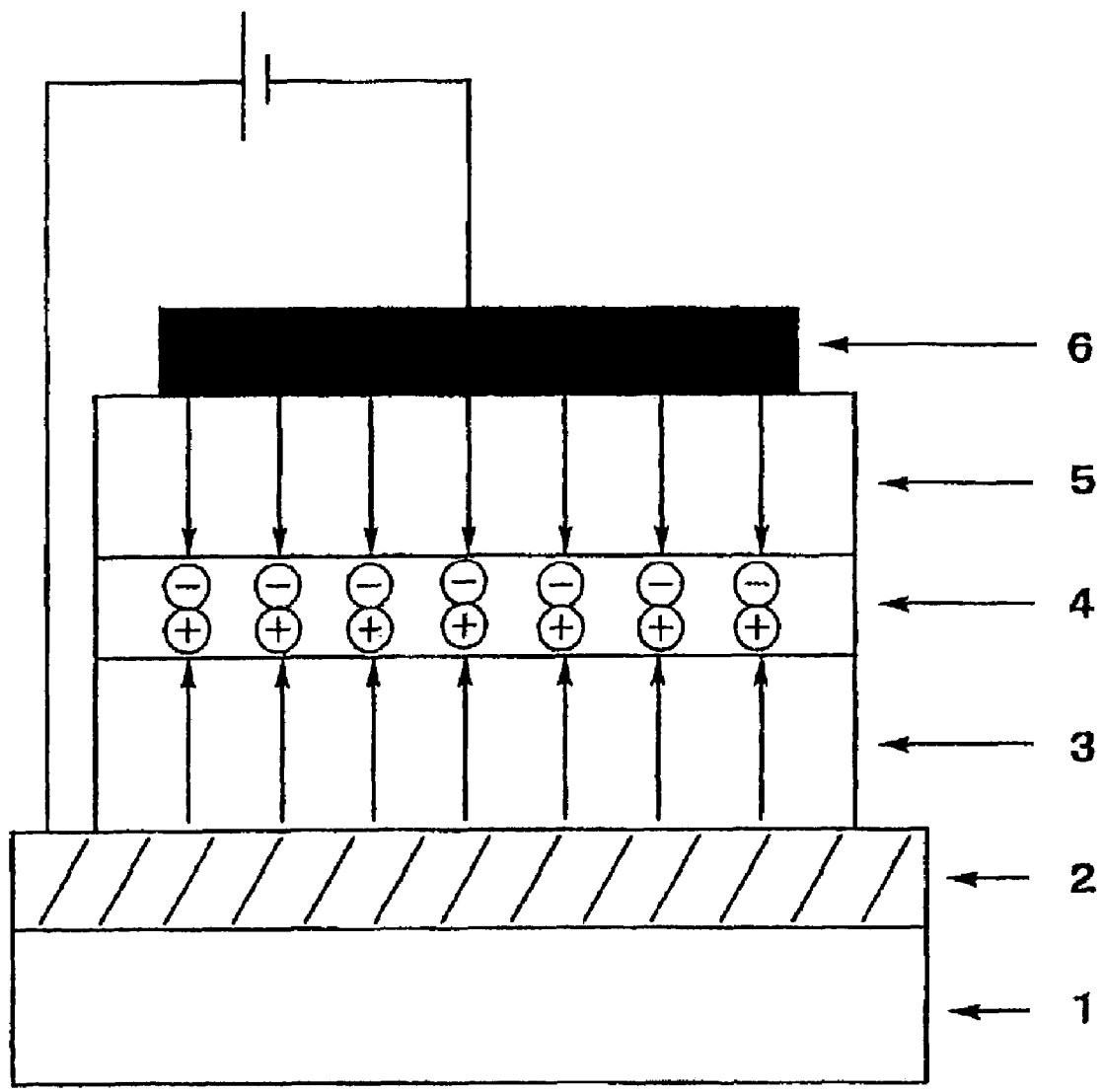
FIG. 1 is a brief figure of one organic EL device according to the present-invention.

The present invention relates to the 4-cyanocoumarin derivatives represented by Formula 1:

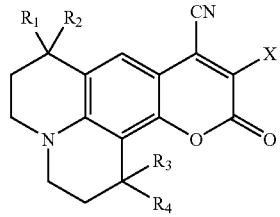

Formula 1

In Formula 1, $R_1$ to $R_4$ independently denote a hydrogen atom, alkyl group, alkoxy group, aliphatic hydrocarbon group or aromatic hydrocarbon group, wherein the hydrocarbon groups optionally have a substituent. When $R_1$ to $R_4$ are alkyl groups, they are selected from those having carbon atoms of up to three, usually, methyl and ethyl groups. Examples of the alkoxy group are those having carbon atoms of up to three, usually, methoxy and ethoxy groups. Depending on use, when $R_1$ to $R_4$ are aliphatic hydrocarbon groups, the chain length is generally selected from those having carbon atoms of up to five, and preferably those having 1 to 4 carbon atoms. The aliphatic hydrocarbon groups may be those in a linear or branching form; examples of such are a methyl, ethyl, vinyl, propyl, isopropyl, 1-propenyl, 2-propenyl, isopropenyl, butyl, isobutyl, sec-butyl, tert-butyl, 2-butenyl, 1,3-butadienyl, pentyl, isopentyl, neopentyl, and 2-pentenyl groups. Examples of the aromatic hydrocarbon group used in the present invention are a phenyl, tolyl, xylyl, biphenyl, naphthyl, anthryl, and phenanthryl groups, which optionally have one or more of substituents. Examples of these substituents are a carboxyl, alkylcarbonyloxy, alkoxy, alkoxycarbonyl, sulfonyl, alkylsulfonyl, aminosulfonyl, hydroxyl, aromatic hydrocarbon, alicyclic hydrocarbon, cyano, 2-butoxyethyl, 2-(2-ethoxy)ethoxyethyl, 2-cyanoethyl, 6-bromohexyl, 2-carboxyethyl, 3-sulfoxypropyl, 4-sulfoxybutyl, 2-hydroxyethyl, phenylmethyl, 4-butoxyphenylmethyl, and 4-butylphenylmethyl groups.

In Formula 1, X denotes a monovalent group, i.e., a hydrogen group, cyano group, nitro group, carboxyl group, aryl group, alkyl group, alkoxy group, heterocyclic group, aliphatic hydrocarbon group, or polycyclic aromatic hydrocarbon group where the heterocyclic groups optionally have one or more substituents. Examples of the aryl group are phenyl, diphenyl, and terphenyl groups. The alkyl group includes, for example, those having carbon atoms of up to three, usually, methyl and ethyl groups. Examples of the alkoxy group are those having carbon atoms of up to three, usually, methoxy and ethoxy groups. The heterocyclic group includes, for example, monocyclic heterocyclic-groups such as heterocyclic five-ring groups which comprise one or more nitrogen, oxygen, sulfur, and/or selenium atoms within their rings; or polycyclic heterocyclic groups formed by condensation of aromatic hydrocarbon groups such as benzene, naphthalene, anthracene, phenanthrene, and pyrene rings. Examples of the heterocyclic groups are monocyclic groups such as a thiazolyl, oxazolyl, imidazolyl group, and triazolyl groups; and polycyclic heterocyclic groups such as a benzothiazolyl, benzoselenazolyl, benzoxazolyl, benzoimidazolyl, naphtothiazolyl, naphtoselenazolyl, naphtoxazolyl, napthoimidazolyl, phenathrothiazolyl, and pyrenothiazolyl groups. These heterocyclic groups optionally have one or more substituents of halogen groups such as a cyano, fluoro, chloro, bromo, and iodo groups; alkoxy groups such as a methoxy and ethoxy groups; aromatic hydrocarbon groups such as an alkoxy, phenyl, bromophenyl, tolyl, xylyl, biphenyl, paphtyl, anthryl, and phenanthryl groups; halogen-substituted aromatic hydrocarbon groups; aromatic hydrocarbon groups such as a methyl, trifluoromethyl, ethyl, propyl, isopropyl, and butyl groups having carbon atoms up to four; and halogen-substituted aliphatic hydrocarbons.

The 4-cyanocoumarin derivatives of the present invention should not be restricted to those having only one 4-cyanocoumarin structure within a molecule as represented by Formula 1, and they may include those having two or more 4-cyanocoumarin structures per one molecule as long as they satisfy the object of the present invention. Of course, these plural structures may be the same or different, or may be symmetric or non-symmetric as the whole molecules. A plurality of 4-cyanocoumarin structures in the same molecule can be linked each other, for example, via characteristic groups containing heteroatoms such as an oxygen, sulfur, and nitrogen atoms, for example, an oxy, thio, imino, and azo groups; or via appropriate-length of aliphatic hydrocarbon groups which may have the above characteristic groups within the chains; or linked via the condensation of heterocyclic groups as represented by Formula 1. These 4-cyanocoumarin derivatives have characteristics of a significantly-high ability of emitting light per molecule and a significantly-high sensitivity to visible light as compared with the compound represented by Formula 1 having a single 4-cyanocoumarin structure within the molecule.

Preferred examples of the 4-cyanocoumarin derivatives of the present invention are the compounds represented by Formulae 3 to 33. For the use in photopolymeric compositions, dye lasers, or organic EL elements, the 4-cyanocoumarin derivatives represented by Formula 1 where $R_1$ to $R_4$ are the same or different aliphatic hydrocarbon groups having one to four carbon atoms, and where X is a polycyclic heterocyclic group having a heterocyclic five-ring within the ring. The compounds, which have the above features and a clear sensitivity to visible light, and emit light in a visible region, such as those represented by Formulae 3, 9, 10, 11, 12 and 28 are extremely useful as photosensitizes for the photochemical condensation of polymeric compounds, laser-active substances in dye lasers, and guests luminous agents for doping host luminescent agents in organic EL elements and for another host luminescent agents.

Formula 3

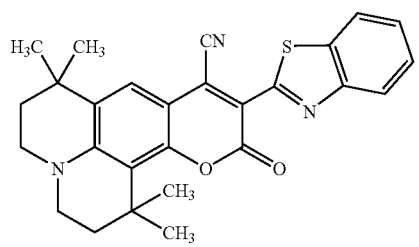

Formula 4

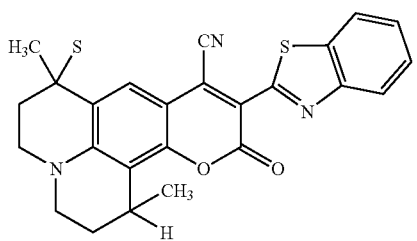

Formula 5

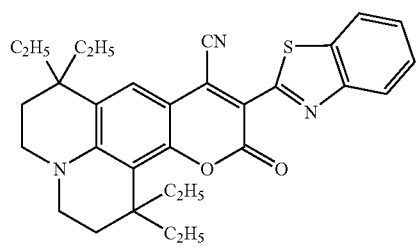

Formula 6

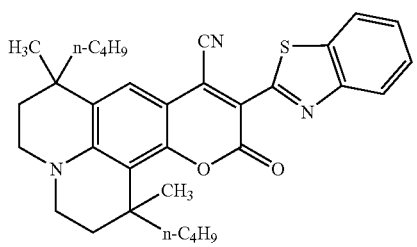

Formula 7

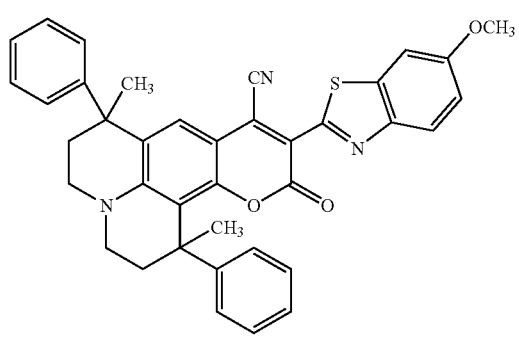

Formula 8

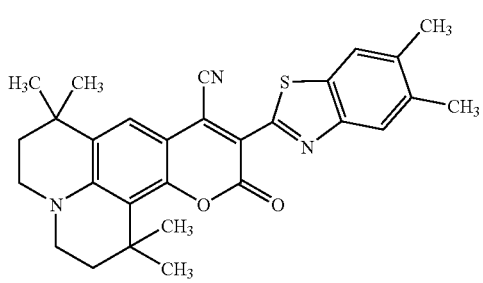

-continued
Formula 9
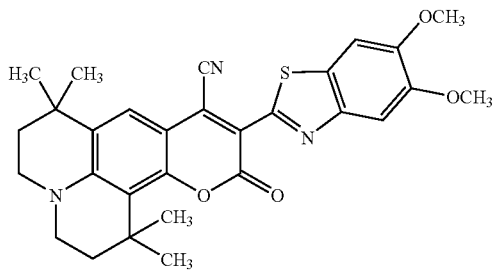
Formula 10
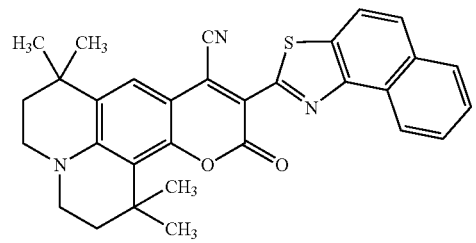
Formula 11
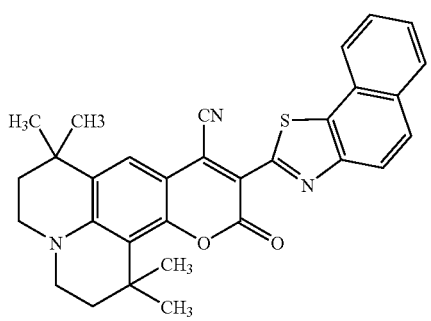
Formula 12
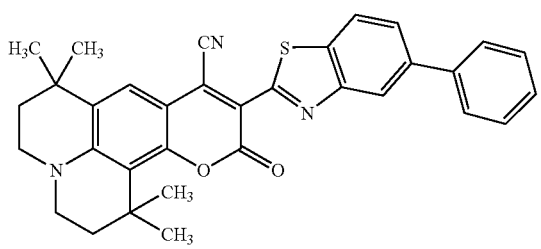
Formula 13
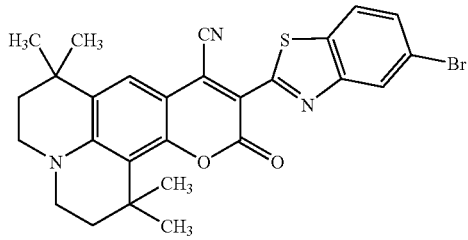
Formula 14
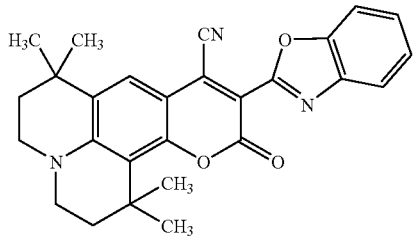
Formula 15
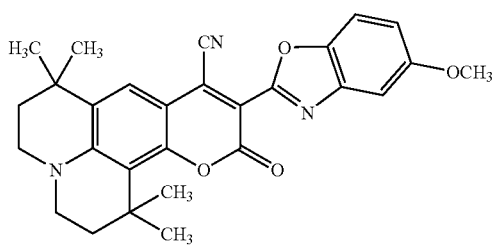
Formula 16
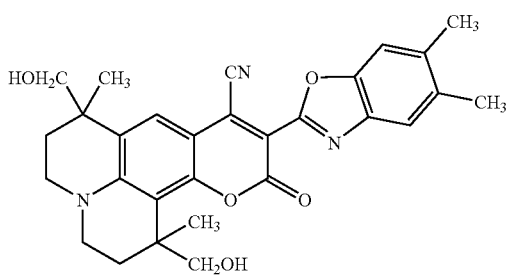
Formula 17
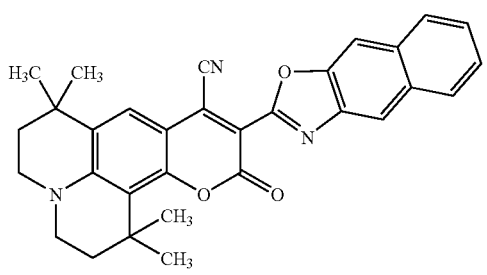
Formula 18
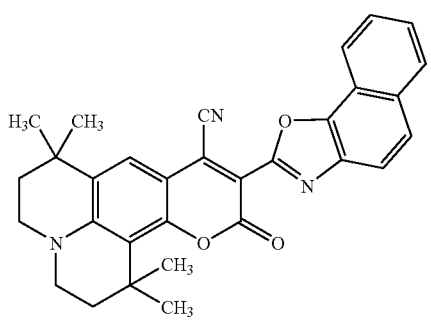

-continued
Formula 19
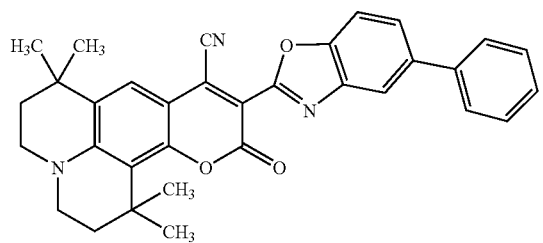
Formula 20
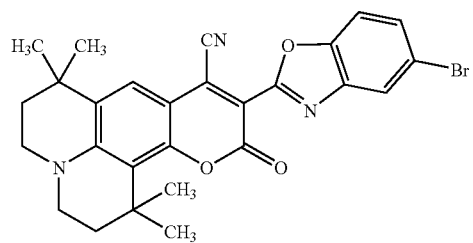
Formula 21
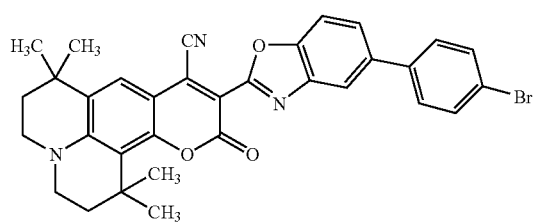
Formula 22
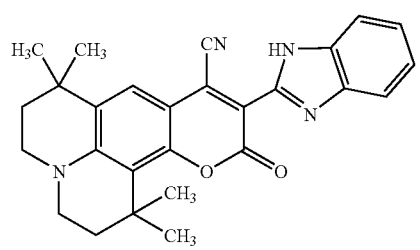
Formula 23
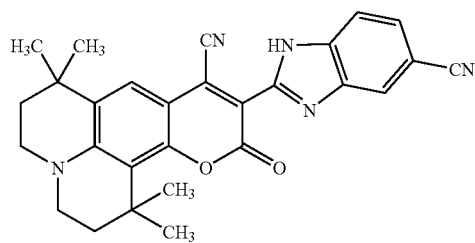
Formula 24
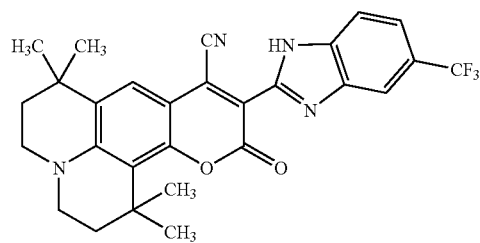
Formula 25
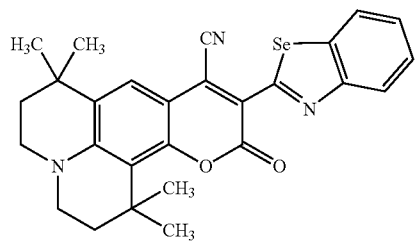
Formula 26
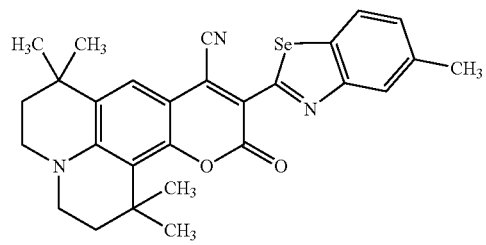
Formula 27
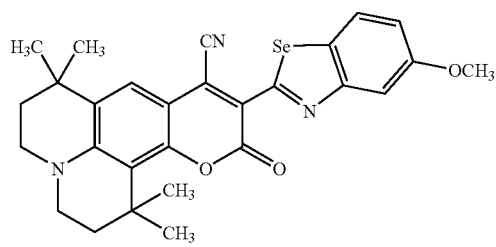
Formula 28
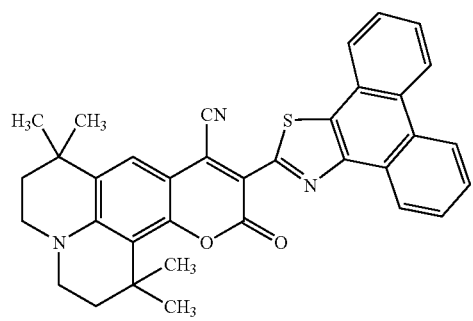

-continued
Formula 29
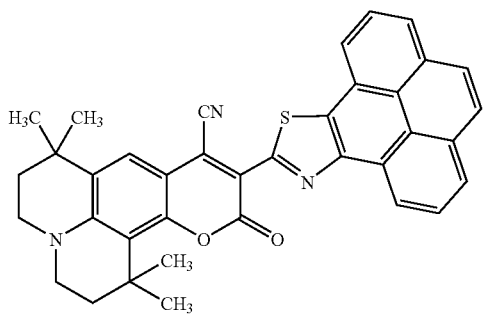
Formula 30
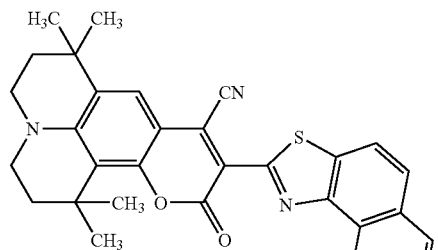
Formula 31
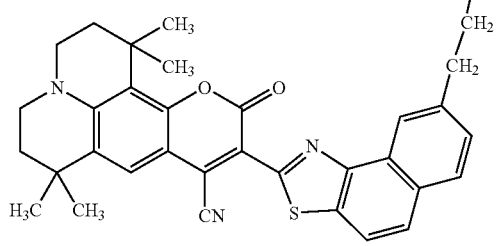
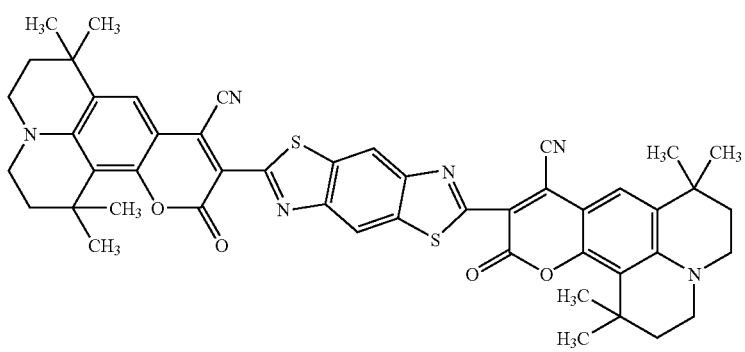
Formula 32
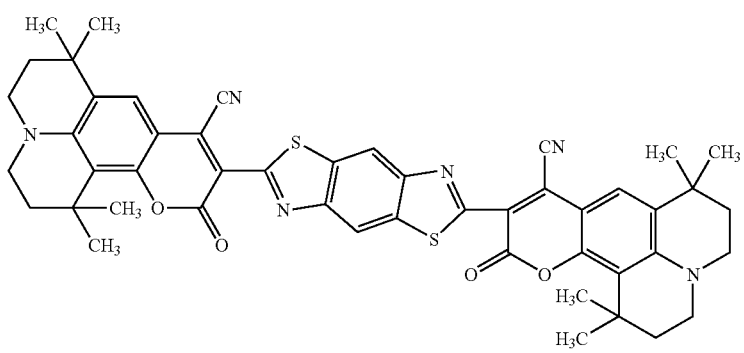
Formula 33
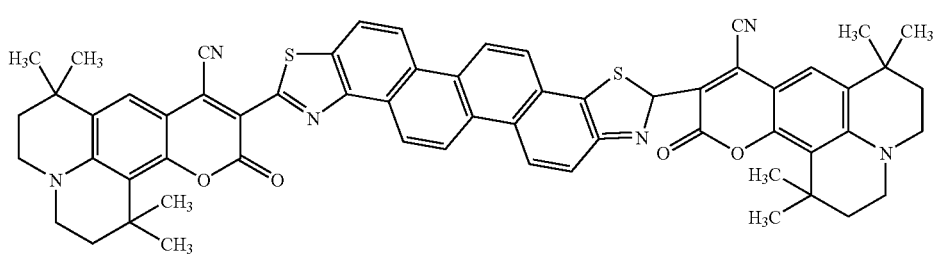

The 4-cyanocoumarin derivatives of the present invention can be prepared by different methods. With an economical viewpoint, preferably used are the methods which produce the derivatives through a step of contacting the compounds, represented by Formula 2 having $R_1$ to $R_4$ which correspond to those in Formula 1, with cyanization agents such as sodium cyanide, potassium cyanide, and cyanohydrin to effect 4-cyanization in a solvent system of a water-soluble solvent(s) such as chloroform, methanol, ethanol, propanol, acetone, ethyl methyl ketone, acetonitrile, propionitrile, tetrahydrofuran, tetrahydropyran, triethylamine, N,N-dimethylformamide, N,N-dimethylacetamide, pyridine, N-methylpyrrolidone, hexamethylphosphoric triamide, sulfolane, and/or dimethylsulfoxide; or in a mixture solutions of water and the water-soluble solvent(s). Any one of the 4-cyanocoumarin derivatives represented by Formulae 3 to 33 can be prepared by the above methods in a desired amount; the compound represented by Formula 2 can be easily prepared by the method disclosed in Japanese Patent Kokai No. 9,892/94, applied for by the same applicant as the present invention.

Formula 2

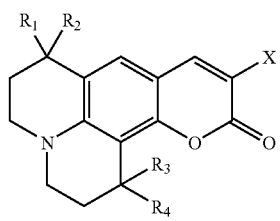

Depending on use, the 4-cyanocoumarin derivatives thus obtained can be used in a reaction mixture form without any further processing, and usually used after purified by the methods generally used in the related compounds thereof such as separation, decantation, filtration, extraction, concentration, thin-layer chromatography, column chromatography, gas chromatography, high-performance liquid chromatography, distillation, sublimation, and crystallization; and if necessary these methods can be used in combination. For use in photosensitizes, the 4-cyanocoumarin derivatives should at least preferably be distilled and/or crystallized prior to use. When used as luminescent agents for organic EL elements or for laser-active substances used in laser oscillation apparatuses, the 4-cyanocoumarin derivatives should preferable be further purified, for example, by sublimation before use.

As described above, the 4-cyanocoumarin derivatives of the present invention are extremely useful as photosensitive agents for polymerizing polymeric compounds with visible light because they have a distinct sensitivity to a longer wavelength of light, particularly visible light, and effectively sensitize polymeric compounds and polymerization initiators. In an actual use, the photosensitizes comprising the 4-cyanocoumarin derivatives of the present invention can be formulated into compositions by combining with materials commonly used in photopolymeric compositions such as polymeric compounds, polymerization initiators, and binding resins. Depending on the types of or the final use of the 4-cyanocoumarin derivatives used, the above polymerization initiators and/or binding resins may be omitted.

The polymeric compounds, for which the photosensitizes of the present invention can be applied, include, for example, monomers, oligomers, prepolymers, and mixtures thereof which contain intermolecularly at least one polymeric-multiple-bond such as an ethylene double bond. Examples of such polymeric compounds are ethyl acrylate, hydroxyethyl acrylate, ethylene glycol dimethacrylate, pentaerythritol triacrylate, pentaerythritol trimethacrylate, polyester methacrylate, polyurethane methacrylate, epoxy methacrylate, etc. The polymeric compounds usable in the photopolymeric compounds of the present invention should not be restricted to the above-mentioned compounds, and should include all the polymeric compounds which can be photopolymerized by the photosensitizes of the present invention.

The polymerization initiators usable in the present invention include organic peroxides such as di-t-butyldioxyisophtalate, 3,3',4,4'-tetrakis(t-butyldioxycarbonyl)benzophenone, ethyl methyl ketone, 2,5-dimethyl-2,5-bis(t-butyldioxy)-3-hexane, di-t-butylhydroperoxide, 2,5-bis(hydroperoxy)-2,5-dimethylhexane, t-butylhydroperoxide, butyl-4,4-bis(t-butyldioxy)valylate, and 1,1-bis(t-butyldioxy)-3,3,5-trimethylcyclohexane; hydrocarbon halides such as 2,4,6-trichloromethyl-s-triazine; and other compounds widely used in photochemical polymerization such as bisimidazole, benzoyl alkyl ether, iron-allene complex, titanocene compound, N-phenylglycine, and diphenyliodonium salt, which can be used in combination, if necessary.

Depending on use, the binding resins usable in the present invention can be those which are commonly used in photopolymeric compositions; poly-N-vinylpyrrolidone, poly (vinyl acetate), poly(vinyl butyral), poly(vinyl carbazole), polystyrene, poly(methyl methacrylate), poly(ethylene oxide), poly(butyl methacrylate), styrene-maleic esther, poly (methyl methacrylate)-methacrylic acid, poly-N-vinylpyrrolidone-glycidyl methacrylate, etc.

The photosensitizes of the present invention comprise one or more specific 4-cyanocoumarin derivatives. To produce photopolymeric compositions by using the photosensitizes, to one part by weight of one of the photosensitizes 1-1,000 parts by weight of, and preferably, 10-500 parts by weight of the aforesaid polymeric compound(s); and optionally up to 1,000 parts by weight of, and preferably up to 500 parts by weight of a biding resin(s), along with 0.1-10 parts by weight of, and preferably 0.5-5 parts by weight of a polymerizing initiator(s). If necessary, the following materials can be appropriately added to the above photopolymeric compositions; quinone or phenol thermal-polymerization-forbidding-agents such as hydroquinone, pyrogallol, 2,6-di-t-butyl-p-cresol, etc.; plasticizers such as saturated and unsaturated carboxylates such as phthalates and adipates; and coloring agents, preservatives, stabilizers, surface protectants, lubricants, suppository coatings, etc.

The photopolymeric compositions of the present invention can be usually used by dissolving in appropriate solvents into solutions, applying the solutions over appropriate support members, and drying the applications. Examples of such solvents include hydrocarbons such as pentane, hexane, cyclohexane, petroleum ether, petroleum benzine, isooctane, benzene, toluene, and xylene; halogen compounds such as carbon tetrachloride, chloroform, 1,2-dichloroethane, 1,2-bromoethane, trichloroethylene, tetrachloroethylene, chlorobenzene, and α-dichlorobenzene; alcohols and phenols such as methanol, ethanol, 1-propanol, 2-propanol, 2,2,2-trifluoroethanol, 1-butanol, 2-butanol, isobutyl alcohol, isopentyl alcohol, cyclohexanol, ethylene glycol, propylene glycol, 2-methoxyethanol, 2-ethoxyethanol, phenol, benzyl alcohol, cresol, diethylene glycol, triethylene glycol, and glycerine; ethers such as diethyl ether, diisopropyl ether, tetrahydrofuran, tetrahydropyran, 1,4-dioxane, anisole, 1,2- dimethoxyethane, diethylene glycol dimethyl ether, dicyclohexyl-18-crown-6, diethylene glycol monomethyl ether, diethylene glycol monoethyl ether, propylene glycol monomethyl ether, and propylene glycol monomethyl ether acetate; ketones such as acetone, ethyl methyl ketone, and cyclohexanone; esters such as ethyl acetate, butyl acetate, ethyl propionate, ethylene carbonate, propylene carbonate, and triethyl phosphate; amides such as formamide, N-methylformamide, N,N-dimethylformamide, N-methylacetamide, N,N-dimethylacetamide, and hexamethylphosphoric triamide; nitriles such as acetonitrile, propionitrile, succinonitrile, and benzonitrile; nitro compounds such as nitromethane and nitrobenzene; amides such as ethylenediamine, pyridine, piperidine, and morpholine; and sulfur compounds such as dimethylsulfoxide and sulfolane. Depending on use, these solvents can be used in combination.

The support members usable in the present invention can be commercially available ones. Depending on use, the followings can be selectively used; metals such as aluminum, magnesium, copper, zinc, chromium, nickel, and iron, as well as alloying sheets thereof; papers such as high-quality papers, art papers, and parting papers; inorganic sheets made of glasses and/or ceramics; and plastic sheets made of poly(ethylene phthalate), polyethylene, poly(m-ethyl methacrylate), poly(vinyl chloride), vinyl chloride/vinylidene chloride copolymer, poly styrene, nylon, cellulose acetate, cellulose acetate, and/or cellulose acetate butylate.

The polymerization methods used in the present invention should not be restricted to specific ones, any of the following techniques can be used; photoinitiation polymerization where light relates only to the initiation step for radical polymerization, ion-polymerization, and ring-opening polymerization; and photo-polyaddition polymerization where light relates to the growing step for polymerization. The lighting source for exposure used in the above techniques may be, for example, sun light, carbon arc, high-pressure mercury lamp, xenon lamp, metal halide lamp, fluorescent lamp, tungsten lamp, argon ion laser, krypton ion laser, helium/cadmium laser, helium neon laser, semiconductor laser, or a commercially available lighting device, which emits visible light with a wavelength of over 400 nm such as a second harmonic of YAG laser.

The present invention also provides the use of the 4-cyanocoumarin derivatives as luminescent agents for organic EL elements. Since the 4-cyanocoumarin derivatives of the present invention emit light in a visible region and mostly have a fluorescent maximum at a wavelength of 600 to 650 nm, particularly, at a wavelength of 610 to 630 nm, they are extremely useful as luminescent agents for organic EL elements that emit visible light in a red-color region. The organic EL elements, for which the 4-cyanocoumarin derivatives can be advantageously applied, are substantially those which comprise organic compounds capable of emitting light, most preferably, multi-layer organic EL elements which usually comprise a cathode to be energized with a positive voltage and an anode to be energized with a negative voltage, a hole injection/transportation layer for injecting holes from the cathode and transporting the injected holes, an electron injection/transportation layer for injecting electrons from the anode and transporting the injected electrons, and a luminous layer for emitting light by recombining the holes and electrons. The 4-cyanocoumarin derivatives, which distinctively emit light and form a stable thin-membrane in a glass state, can be advantageously used as host luminescent agents for organic EL elements. Most of the 4-cyanocoumarin derivatives of the present invention function as materials for hole injection/transportation layers and electron injection/transportation layers, and also function as guest luminescent agents for improving luminescent efficiency and luminescent spectra by doping in a small amount to another host luminescent agents such as metal complexes containing 8-quinols as a ligand such as tris-(8-quinolinolato)aluminum. Thus, when used in organic EL elements which inevitably require at least one of these materials, the derivatives of the present invention can be advantageously used alone or in combination with another luminescent agents such as dicyanomethylene, coumarin, perylene, rubrene, and their related compounds; and materials for hole or electron injection/transportation. In multi-layer organic EL elements, when luminescent agents have also a hole or electron injection/transportation ability, a hole or electron injection/transportation layer can be omitted. While, when materials for a hole injection/transportation layer have also an electron injection/transportation ability, corresponding electron injection/transportation layer can be omitted and vice versa.

The organic EL elements of the present invention is applicable for both mono- and multi-layer organic EL elements. The operation of organic EL elements consists essentially of the following steps of injecting electrons and holes from electrodes, transporting the injected electrons and holes through solids, recombining the transported electrons and holes to induce singlet- or triplet-excitation, and allowing the excitons to emit light. These steps essentially do not differ both in the mono- and multi-layer organic EL elements. However, in the monolayer organic EL elements, the features of the above four steps can be improved only by altering the molecular structure of luminescent agents. While the multi-layer organic EL elements, which can allot the functions required in each step to a plurality of materials and independently optimize the materials, are generally composed into a multi-layer form rather than a monolayer form for ease of attaining the desired functions.

Now explaining the organic EL element of the present invention with reference to a multi-layer organic EL element, FIG. 1 outlines the multi-layer organic EL element according to the present invention. In FIG. 1, the reference numeral 1 is a substrate made of a conventional substrate materials, for example, glasses such as soda-, barium silicate-, and aluminosilicate glasses; and plastics and ceramics. Preferable examples of such are transparent glasses and plastics and opaque ceramics such as silicones which can be used in combination with transparent electrodes.

The reference numeral 2 is a anode which is usually closely attached onto either side of a substrate 1 and then coated with a conductive material, which has a relatively low electrical-resistance and a relatively high optical-transmittance through over the visible region, to form a layer of 10 to 1,000 nm in thickness. The conductive material usually includes metals such as gold, platinum, and nickel; metal oxides such as tin oxide, indium oxide, and mixture systems thereof (abbreviated as "ITO" hereinafter); conductive oligomers and polymers with a repeating unit of aniline, thiophene, or pyrrole. Among these conductive materials, ITO has advantageous features that it can be easily formulated into those with a relatively low conductivity, and minute patterns can be easily formed thereupon.

The reference numeral 3 is a hole injection/transportation layer and, by the method similarly as in the anode 2, it is usually attached closely onto the anode 2 and then coated, for example, with aromatic tertiary amine, hydrazone, carbazole, or a derivative thereof to form a layer of 1 to 1,000 nm in thickness. Examples of the aromatic tertiary amine are triphenylamines such as N,N'-bis(3-methylphenyl)-N,N'-diphenyl-(1,1'-biphenyl)-4,4'-diamine, and N,N'-di(1-naphthyl)-N,N'-diphenyl-[1,1'-biphenyl]-4,4'-diamine (abbreviated as "NPB" hereinafter), and polymers thereof; and those with spiro centers intramolecularly or n electron system starburst molecules such as triarylamine.

The reference numeral 4 is a luminous layer and, similarly as the method in the anode 2, it is usually attached closely onto the hole injection/transportation layer 3, and then coated with a luminescent agent to form a layer of 10 to 1,000 nm, preferably, 10-200 nm in thickness. The luminescent agent includes those which have a relatively-high fluorescent quantum yield, for example, the 4-cyanocoumarin derivatives represented by Formula 1, and other conventional oxathiazole, phenanthrene, triazole derivatives, quinaqulidone, rubulene, and derivatives thereof, as well as metal complexes of quinoline derivatives such as 8-hydroxyquinoline and metals such as aluminum, zinc, and beryllium. These luminescent agents can be used alone or in an appropriate combination. In the case of using the 4-cyanocoumarin derivatives represented by Formula 1 as a guest luminescent agent, it can be usually used in an amount of at least 0.01 mole percentage, preferably, 0.1-10 mole percentage to a host luminescent agent, varying depending on the type of the host used.

The reference numeral 5 is an electron injection/transportation layer and, similarly as in the anode 2, it is usually attached closely onto the luminous layer 4, and then coated with either a similar compound as used in the luminous layer 4 or a cyclic ketone such as benzoquinone, anthraquinone, or fluorenone, or a derivative thereof to form a thin layer of 10 to 500 nm in thickness.

The reference numeral 6 is a cathode and is prepared by closely attaching onto the electron injection/transportation layer 5 and then deposited with a metal such as lithium, magnesium, calcium, sodium, silver, aluminum, or indium, which can be used alone or in an appropriate combination and which has a work function (usually 6 eV or lower) lower than that of the compound used in the electron injection/transportation layer 5; or prepared by combining with an ITO electrode and a buffer layer such as copper phthalocyanine. The thickness of the cathode 6 is not specifically restricted and usually it is set to give a thickness of at least 100 nm in view of the conductivity, production cost, total thickness of a final electrode, light transmissibility, etc. To improve the efficiency of electron injection, for example, a thin layer made of an alkaline metal or alkaline earth metal can be provided between the electron injection/transportation layer 5 and the cathode 6.

As described above, the organic EL element of the present invention can be obtained by closely attaching together adjacent layers onto the substrate 1 the anode 2, cathode 6, and luminous layer 4, and if necessary, the hole electron injection/transportation 3 and the electron injection/transportation 5 for their systematic formulation. When formulating each layer, it should preferably be handled under a relatively high level of vacuum conditions, particularly, $10^{-5}$ Torr or lower through over the processing to reduce the oxidation and decomposition of organic compounds and the adsorption of oxygen and moisture as low as possible. In the case of forming the luminous layer by combining the host- and the guest-luminous agents, the ratio of these agents in the luminous layer is controlled either by previously mixing them in a prescribed amount or independently controlling their heating temperature when deposited in vacuo. The organic EL element thus formulated should preferably be sealed partly or wholly, for example, with sealing glasses or metal caps; or coated with protective membranes such as ultraviolet hardening resins.

Referring to the organic EL element in FIG. 1, when a DC current is energized between the anode 2 and the cathode 6, the hole injected from the anode 2 is transported to the luminous layer 4 through the hole electron injection/transportation layer 3, while the electron injected from the cathode 6 is transported to the luminous layer 4 through the electron injection/transportation layer 5, resulting in a rebinding of holes and electrons in the luminous layer 4 to emit a prescribed wavelength of light from the excited luminous agents through the anode 2 and the substrate 1. In this case, a white luminous is obtainable by coexisting both emissions from the host- and the guest-luminous agents.

Now explaining the use of the organic EL element of the present invention, it is actuated by temporally energizing with a relatively high voltage pulse direct current voltage or continuously energizing a relatively low voltage non-pulse direct current voltage. Since the organic EL element of the present invention emits a light with a satisfactory color purity in a red-color region and has advantageous features in luminescent efficiency and durability, it has a variety of uses in luminous bodies and apparatuses including devices, equipments, instruments, machines, etc., (designated as "apparatuses" hereinafter) for visually expressing information. Since the luminous bodies, having the organic EL element of the present invention as a luminous source, have a relatively low wattage and can be constructed into a relatively low weight plain plate, they can be used as a less energy costuming and compact luminous sources for lighting devices in general and others such as liquid crystal elements, copying devices, printing devices, electric photo devices, computers, and related apparatuses; industrial controlling apparatuses, electric measurements, instruments in general, communicating apparatuses, machines of electric measurement for medical use, machines equipped with automobiles, ships, and space ships, apparatuses for controlling aircraft, interiors, signboards, and signs/marks. When used in information displays for computers, televisions, video recorders, game apparatuses, watches/clocks, car navigation systems, oscilloscopes, radars, and sonars, the organic EL element of the present invention can be actuated alone or in combination with an organic EL element(s) which emits light in a green- or blue-color region, and if necessary, further actuated by processing into the form of a display panel and then applying thereupon conventional single- and active-matrix systems.

In the case of using the 4-cyanocoumarin derivatives of the present invention in dye lasers, they are purified similarly as in conventional dye-laser-active-substances, and then dissolved in appropriate solvents, and if necessary, after adjusted to appropriate pH levels, enclosed in dye cells in laser oscillating apparatuses. The 4-cyanocoumarin derivatives have characteristics of a relatively-wide range of stage gains in a visible region, satisfactorily-high light tolerance, and desirable quality-durability even after a relatively-long period of time of use.

The following Examples 1 to 6 describe the 4-cyanocoumarin derivatives according to the present invention, and Examples 7 to 9 describe the EL elements using the derivatives, display panels using the organic EL elements, and information displays using the display panels according to the present invention:

EXAMPLE 1

4-Cyanocoumarin Derivative

Five grams of 9-formyl-8-hydroxy-1,1,7,7-tetramethyl julolidine, represented by Formula 34, and 1.7 g cyanoacetamide were dissolved by heating in methanol. To the solution was added 0.38 ml piperidine, and the mixture was allowed to react for three hours under heating reflux conditions and cooled to ambient temperature. The precipitated 4.1 g crystals of an amide compound represented by Formula 35 were filtered, admixed with 2.9 g o-aminothiophenol and 10 ml N,N-dimethylformamide, and reacted at 110° C. for six hours. After cooling to ambient -temperature, the reaction mixture was admixed with 30 ml isopropyl ether. The formed 4.1 g crystals were collected and dissolved by heating in 300 ml acetone, followed by filtering the solution and distilling the filtrate to remove a half of the acetone. The condensed solution was cooled, and the newly precipitated crystals were filtered, washed with isopropyl ether, and dried to obtain 3.5 g crystals of a compound represented by Formula 36 with a benzothiazolyl group bound to the C-3 position.

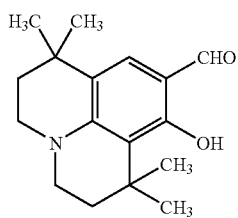

Formula 34

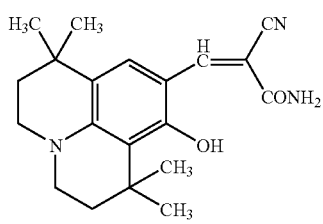

Formula 35

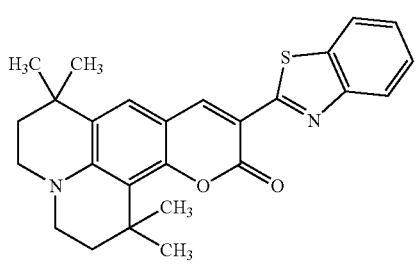

Formula 36

2.3 g of the compound represented by Formula 36 were placed in a reaction vessel, dispersed in 33 ml N,N-dimethylformamide, admixed with 2.53 ml of a 30 w/w % aqueous sodium cyanide drop by drop, reacted for one hour, and further admixed with 0.44 ml bromine drop by drop while cooling to 0-10° C., followed by stirring for two hours. The formed crystals were collected by filtering, washed with water, dried, and purified by silica gel chromatography using chloroform as a developer to obtain 2.1 g glittering green-colored crystals of a 4-cyanocoumarin derivative represented by Formula 3.

Conventional measurement revealed that the 4-cyanocoumarin derivative of this example had a melting point of 266-269° C. and showed the absorption maximum and the fluorescent maximum at wavelengths of 564 nm and 614 nm, respectively, when measured in methylene chloride. On measurement of $^1$H-nuclear magnetic resonance spectrum (hereinafter abbreviated as "$^1$H-NMR") in chloroform deuteride, the compound showed a chemical shift δ (ppm, TMS) at peaks of 1.37 (6H, s), 1.59 (6H, s), 1.80 (2H, t), 1.85 (2H, t), 3.36 (2H, t), 3.45 (2H, t), 7.39-7.44 (1H, m), 7.52-7.61 (1H, m), 7.72 (1H, s), 7.96 (1H, d), and 8.18 (1H, d).

EXAMPLE 2

4-Cyanocoumarin Derivative

To 19 g of the amide compound represented by Formula 35, obtained by the method in Example 1, were added 9.2 g of 1-amino-2-thionaphthol and 50 ml N,N-dimethylformamide, followed by a reaction at 110° C. for four hours. Thereafter, the reaction mixture was cooled to ambient temperature, and the formed crystals were filtered for collection. The crystals were dissolved in 60 ml chloroform, filtered, and recrystallized in 140 ml methanol. The newly formed crystals were collected by filtering and dried to yield 18.2 g crystals of a compound represented by Formula 37.

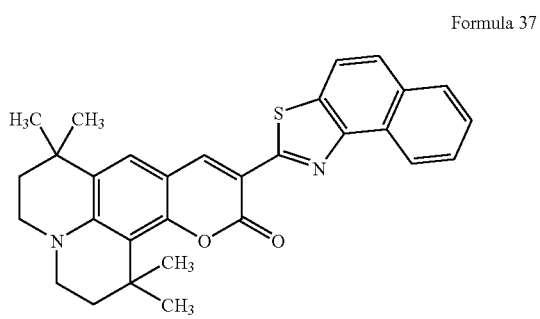

Formula 37

Five grams of the compound represented by Formula 37 were placed in a reaction vessel, dispersed in 50 ml N,N-dimethyl-formamide, admixed with 3.4 ml of a 30 w/w % aqueous sodium cyanide solution drop by drop, and reacted for one hour. To the reaction mixture was added drop by drop 0.59 ml bromine under cooling conditions at 0-10° C., followed by stirring for two hours. 4.9 g of the formed crystals were collected by filtering, washed with water, dried, and recrystallized in N,N-dimethylformamide to obtain 2.6 g glittering green-colored crystals of a 4-cyanocoumarin derivative represented by Formula 10.

Conventional measurement revealed that the 4-cyanocoumarin derivative in this example had a melting point of 322-326° C. and showed the absorption maximum and the fluorescent maximum at wavelengths of 580 nm and 627 nm, respectively, when measured in methylene chloride. On measurement of $^1$H-NMR in chloroform deuteride, the compound showed a chemical shift δ (ppm, TMS) at peaks of 1.40 (6H, s), 1.60 (6H, s), 1.81 (2H, t), 1.87 (2H, t), 3.36 (2H, t), 3.45 (2H, t), 7.58-7.63 (1H, m), 7.71-7.76 (1H, m), 7.79 (1H, s), 7.81-7.84 (1H, m), 7.94-7.99 (2H, m), and 9.01 (1H, d).

EXAMPLE 3

4-Cyanocoumarin Derivative

To 3.4 g of the amide compound represented by Formula 35, obtained by the method in Example 1, were added 3.0 g of 2-amino-4-phenylthiophenol and 30 ml N,N-dimethylformamide, followed by a reaction at 140° C. for four hours. Thereafter, the reaction mixture was cooled to ambient temperature, and the formed crystals were collected by filtering. The crystals were dissolved in 30 ml chloroform, filtered, and admixed with 70 ml methanol. The newly formed crystals were collected by filtering and dried to yield 2.5 g crystals of a compound represented by Formula 38.

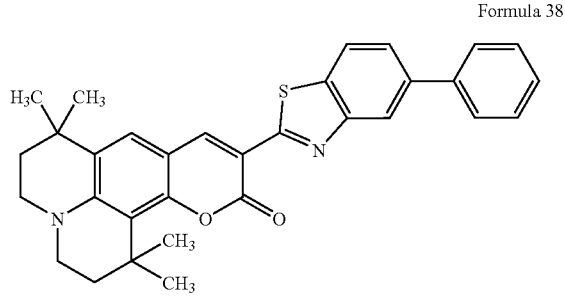

Formula 38

Two and half grams of the compound represented by Formula 38 were placed in a reaction vessel, dispersed in 25 ml N,N-dimethylformamide, admixed drop by drop with 1.6 ml of a 30 w/w % aqueous sodium cyanide solution, and reacted for one hour. To the reaction mixture was added drop by drop 0.31 ml bromine under cooling conditions at 0-10° C., followed by stirring for two hours. The formed crystals were collected by filtering, washed with water, dried, and purified by silica gel column chromatography using chloroform as a developer to obtain 1.9 g glittering green-colored crystals of a 4-cyanocoumarin derivative represented by Formula 12.

Conventional measurement revealed that the 4-cyanocoumarin derivative in this example had a melting point of 261-263° C. and showed the absorption maximum and the fluorescent maximum at wavelengths of 569 nm and 617 nm, respectively, when measured in methylene chloride. On measurement of $^1$H-NMR in chloroform deuteride, the compound showed a chemical shift δ (ppm, TMS) at peaks of 1.38 (6H, s), 1.58 (6H, s), 1.81 (2H, t), 1.85 (2H, t), 3.36 (2H, t), 3.45 (2H, t), 7.26-7.41 (1H, m), 7.46-7.51 (2H, m), 7.66-7.69 (1H, dd), 7.71-7.75 (3H, m), 8.01 (1H, d), and 8.39 (1H, d).

EXAMPLE 4

4-Cyanocoumarin Derivative

To 3.0 g of the amide compound represented by Formula 35, obtained by the method in Example 1, were added 3.0 g of 2-amino-4,5-dimethoxythiophenol and 15 ml N,N-dimethylformamide, followed by a reaction at 140° C. for four hours. Thereafter, the reaction mixture was cooled to ambient temperature, and the formed crystals were collected by filtering. The crystals were dissolved in chloroform and purified by silica gel chromatography using a mixture solution of chloroform and ethyl acetate as a developer to yield 2.5 g crystals of a compound represented by Formula 39.

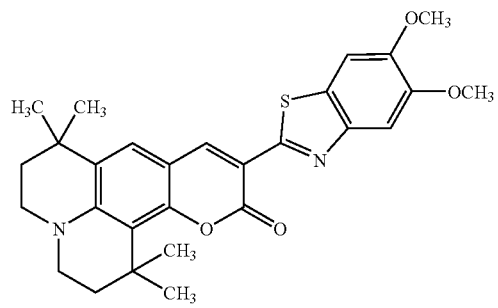

Formula 39

Two and half grams of the compound represented by Formula 39 were placed in a reaction vessel, dispersed in 50 ml N,N-dimethylformamide, admixed with 2.0 ml of a 30 w/w % aqueous sodium cyanide solution drop by drop, and reacted for one hour. To the reaction mixture was added drop by drop 0.25 ml bromine under cooling conditions at 0-10° C., followed by stirring for two hours. The formed crystals were collected by filtering, washed with water, dried, dissolved in chloroform, and purified by silica gel column chromatography using a mixture solution of chloroform and ethyl acetate as a developer to obtain 1.1 g glittering green-colored crystals of a 4-cyanocoumarin derivative represented by the Formula 9.

Conventional measurement revealed that the 4-cyanocoumarin derivative in this example had a melting point of 308-312° C. and showed the absorption maximum and the fluorescent maximum at wavelengths of 576 nm and 629 nm, respectively, when measured in methylene chloride. On measurement of $^1$H-NMR in chloroform deuteride, the compound showed a chemical shift δ (ppm, TMS) at peaks of 1.32 (6H, s), 1.60 (6H, s), 1.77 (2H, t), 1.83 (2H, t), 3.29 (2H, t), 3.37 (2H, t), 3.98 (6H, s), 7.36 (1H, s), 7.49 (1H, s), and 7.61 (1H, s).

For the 4-cyanocoumarin derivatives obtained either by the methods in Examples 1 to 4 or in accordance therewith, the properties of the derivatives are tabulated in Table 1. In Table 1, the wavelengths of the absorption maxima of the derivatives were determined after dissolved in methylene chloride, while the fluorescent maxima of the derivatives were determined at a concentration of $10^{-7}$ M in methylene chloride. As controls; compounds represented by Formulae 36 to 39 having the coumarin skeleton were used as related compounds of the above derivatives.

TABLE 1

| Compound | Absorption maximum (nm) | Fluorescent maximum (nm) | Melting point (° C.) | Remarks |
|---|---|---|---|---|
| Formula 3 | 564 | 614 | 266-269 | Present invention |
| Formula 9 | 576 | 629 | 308-312 | Present invention |
| Formula 10 | 580 | 627 | 322-326 | Present invention |
| Formula 11 | 575 | 622 | 302-307 | Present invention |
| Formula 12 | 569 | 617 | 261-263 | Present invention |
| Formula 28 | 586 | 631 | 329-337 | Present invention |
| Formula 36 | 479 | 509 | 224-227 | Control |
| Formula 37 | 489 | 516 | 274-278 | Control |
| Formula 38 | 483 | 511 | 230-234 | Control |
| Formula 39 | 486 | 518 | 263-265 | Control |

As shown in Table 1, the absorption maxima of 4-cyanocoumarin derivatives of the present invention clearly shifted to the side of a longer wavelength as compared with those of the control compounds. All the 4-cyanocoumarin derivatives represented by Formulae 3, 9, 10, 11, 12 and 28 gave absorption maxima nearness to the wavelength of commercially available lighting sources, e.g., a second harmonic of 532 nm of YAG laser. This shows that the 4-cyanocoumarin derivatives of the present invention are useful as photosensitizes for polymerizing polymeric compounds with visible light. The 4-cyanocoumarin derivatives represented by Formulae 3, 9, 10, 11, 12 and 28 emitted light in a visible region and showed luminescent maxima, the wavelengths of which were clearly longer than those of the related compounds represented by Formulae 36 to 39. The fact shows that the 4-cyanocoumarin derivatives of the present invention are useful as laser-active substances for dye lasers and as luminescent agents for organic EL elements.

Depending on the structures of the 4-cyanocoumarin derivatives of the present invention, the materials, reaction conditions, and yields thereof are differed, and the derivatives including those represented by Formula 3 to 33 are easily prepared in a desired amount by the methods in Examples 1 to 4 or those in accordance therewith.

EXAMPLE 5

Photopolymeric Composition

According to a usual manner, 900 parts by weight of ethylene glycol monoethyl ether were mixed with 100 parts by weight of pentaerythritol acrylate as a photopolymeric monomer, 100 parts by weight of a copolymer of acrylic acid and methacrylic acid as a binding resin, and eight parts by weight of 3,3',4,4'-tetra(t-butylperoxycarbonyl)benzophenone, and further mixed with, as a photosensitizer, six parts by weight of either of the 4-cyanocoumarin derivatives obtained by the methods in Examples 1 and 2. Thus, two types of photopolymeric compositions were obtained.

According to a usual manner, the obtained compositions were homogeneously applied over an aluminum plate, which the surface had been set by sand, to form a photosensitive layer, followed by forming a poly(vinyl alcohol) layer over the photosensitive layer to prevent the polymerization-inhibition by oxygen. A glazing scale was closely attached to the photosensitive layer and a 3 kW super-high pressure mercury lamp was provided, and the layer was irradiated by a light of a wavelength of 532 nm, which corresponded to a second harmonic of YAG laser, emitted by the lamp using in combination with "Y47" and "Y52", sharp cult filters commercialized by Toshiba Glass Kabushiki-Kaisha, Tokyo, Japan; "KL49" and "KL54", interference filters commercialized by Toshiba Glass Kabushiki-Kaisha, Tokyo, Japan; and "HA30", a heat-ray-cut-filter commercialized by HOYA Corporation, Tokyo, Japan. Thereafter, the irradiated layer was in a usual manner developed in an alkaline developer, followed by calculating the sensitivity based on the step number at which the compositions were photo-cured in such a manner that, in the numerical formula represented by Equation 1, transmittance Tn of the step number "n" of a step tablet, exposure time t, and exposure strength Io were respectively substituted for the equation. In parallel, in place of the 4-cyanocoumarin derivatives of the present invention, there provided systems using related compounds represented by Formulae 36 and 37 and having a similar skeleton as in the derivatives of the present invention represented by Formulae 3 and 10, except that the cyano group at the 4-position of the derivatives was replaced with hydrogen. These related compounds were similarly treated as above for controls. The results are in Table 2.

Equation 1

$$E(mJ/cm^2)=Io(Mj/cm^2.s) \times Tn \times t(s)$$

TABLE 2

| Compound | Wavelength, measured (nm) | Sensitivity (Mj/cm$^2$) | Remarks |
| --- | --- | --- | --- |
| Formula 3 | 532 | 0.26 | Present invention |
| Formula 10 | 532 | 0.27 | Present invention |
| Formula 36 | 532 | 1.70 | Control |
| Formula 37 | 532 | 0.32 | Control |

As evident from the results in Table 2, both the 4-cyanocoumarin derivatives represented by Formulae 3 and 10 of the present invention had a significantly higher sensitivity than those of the controls, when measured at a wavelength of 532 nm. This indicates that the derivatives of the present invention can be advantageously used to sensitize polymeric compounds and polymerization initiators.

EXAMPLE 6

High-purity 4-cyanocoumarin Derivative

The 4-cyanocoumarin derivatives of the present invention, obtained by the methods in Examples 1 to 4, were in a usual manner sublimated for purification into more highly-purified 4-types of 4-cyanocoumarin derivatives represented by Formulae 3, 9, 10 and 12.

The derivatives thus obtained are useful as luminescent agents in organic EL elements and laser-active substances for dye lasers.

EXAMPLE 7

Organic EL Element

A glass substrate, having a transparent ITO electrode with 100 nm in thickness, which had been patternized with vaporized aqua regia, was ultrasonically washed with a neutral detergent, refined water, and isopropyl alcohol. The substrate was removed from the boiling isopropyl alcohol, dried, washed with ultraviolet ozone, and then fixed to a vaporization apparatus, followed by reducing the atmospheric pressure to $10^{-7}$ Torr. Thereafter, NPB was deposited onto the surface, having the transparent ITO electrode as an electrode on the glass substrate, up to give a thickness of 60 nm to form a hole electron injection/transportation layer. Then, a cathode was formed on the hole electron injection/transportation layer by co-depositing, while monitoring the thickness by a sensor for membrane thickness, on the layer either of the 4-cyanocoumarin derivatives of Formulae 3, 9, 10 and 12, obtained by the methods in Examples 1 to 4, and tris(8-hydroxyquinoline)aluminum (abbreviated as "Alq3" hereinafter) in a weight ratio of 0.8:100 up to give a thickness of 20 nm to form a luminous layer; depositing Alq3 on the luminous layer up to give a total thickness of 40 nm to form an electron injection/transportation layer; and further sequentially depositing lithium fluoride and aluminum on the electron injection/transportation layer up to give a thickness of 0.5 nm and 150 nm, respectively. Finally, under nitrogen atmospheric conditions, the resulting elements were totally sealed with a glass plate and an ultraviolet ray hardening resin to obtain four types of organic EL elements.

These organic EL elements thus obtained were tested for luminous property in a usual manner. In parallel, as a control, similarly as in the above except for substituting the compound represented by Formula 40 for the 4-cyanocoumarin derivatives, an organic EL element was prepared and then treated similarly as in those with the 4-cyanocoumarin derivatives. The results are in Table 3.

TABLE 3

Formula 40

[Chemical structure of Formula 40: a pyran ring with two CN groups, H₃C, and a styryl group connected to a phenyl ring with N(CH₃)₂]

| Compound | Luminescent maximum wavelength (nm) | Luminance (cd/m²)*¹ | Life time (hr)*² | Remarks |
|---|---|---|---|---|
| Formula 3 | 625 | 11 | 90 | Present invenrion |
| Formula 8 | 643 | 85 | 50 | Present invention |
| Formula 10 | 640 | 141 | 512 | Present invention |
| Formula 12 | 630 | 120 | 544 | Present invention |
| Formula 40 | 600 | 80 | 16 | Control |

*¹Values measured when actuated with a current of 11 mA/cm².
*²Half life when actuated with a constant current at an initial luminance of 300 cd/m².

As evident from the results in Table 3, the organic EL elements in this example emitted a red-color light having a luminescent maximum wavelength in a visible region with wavelengths over 600 nm, particularly, wavelengths of 620 to 650 nm. The emission was observed at about four volts and the maximum luminance of 6,000 cd/m² was at about 15 V. The half-period of the luminescent of the organic EL elements of the present invention when actuated with a constant current at an initial luminance of 300 cd/m² were substantially the same as that of control or far exceeded the control, i.e., 100 hours or more. No dark spot was observed even after a lapse of 100 hours from the luminous initiation. As evident from the results in Table 3, the organic EL element as a control had a luminescent maximum wavelength with a shorter wavelength, i.e., 600 nm, and the luminescent color was almost orange when observed macroscopically.

These results show that the organic EL elements of the present invention in this example are red-color luminous elements with a satisfactory color purity.

EXAMPLE 8

Display Panel

Figure 2:
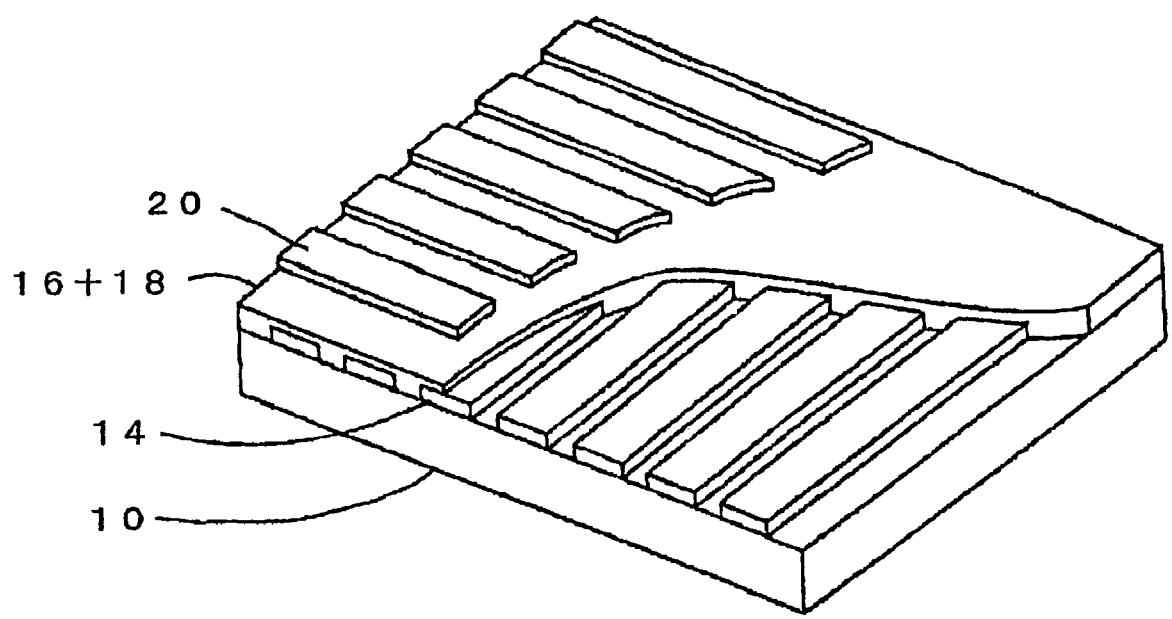
FIG. 2 is a brief figure of one display panel according to the present invention.

FIG. 2 is a single-matrix-type display panel which is constructed mainly with the organic EL element of the present invention and which has 20 lines of electrodes in the horizontal direction and 30 lines of electrodes in the vertical direction. The display panel is prepared as follows:

In accordance with the method in Example 7, the anode 14 was formed on either side of a glass plate 10 using the transparent ITO electrode and processed into a stripe shape by the wet-etching method. Then, in accordance with the method in Example 7, a hole electron injection/transportation layer 16 and a luminous layer 18 were sequentially installed in the above glass substrate 10, while a cathode 20 was processed into a stripe shape by using a mechanical mask. Thereafter, the resulting organic EL element was sealed with a glass plate, not shown in the figure, and an ultraviolet hardening resin. In the display panel in this example, a radiator plate or cooling fan can be installed in the back of the cathode 20, if necessary.

EXAMPLE 9

Information Display

Figure 3:
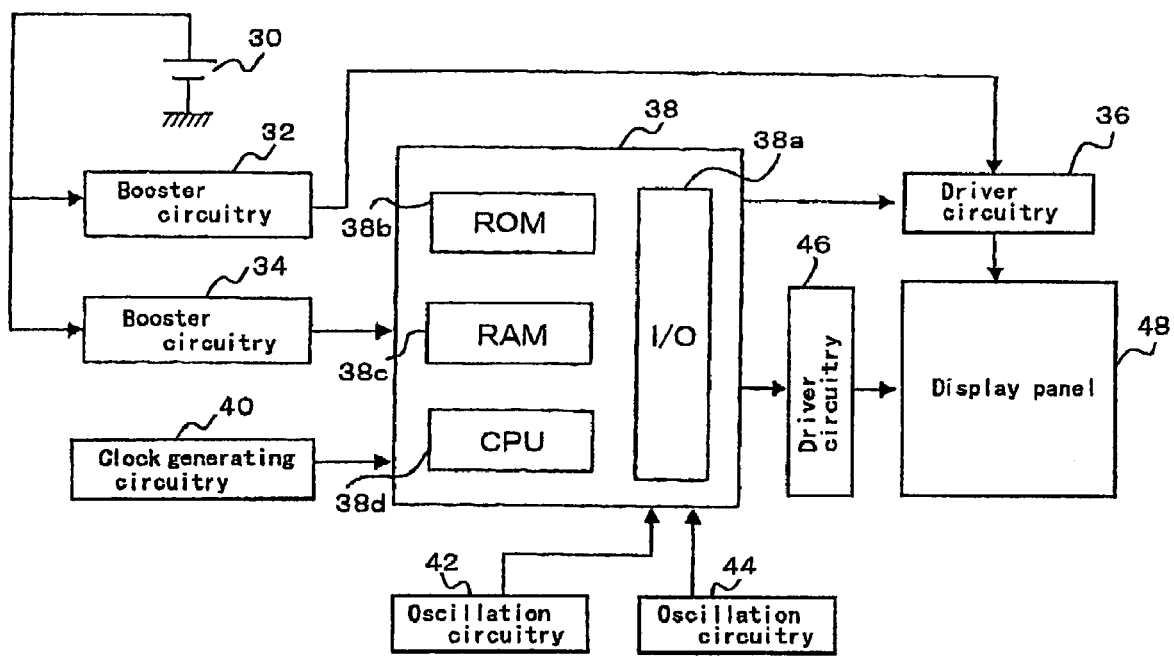
FIG. 3 is a block diagram of one information display according to the present invention.

FIG. 3 is an information display with a display panel prepared by the method in Example 8. In FIG. 3, the reference numeral 30 is a direct-current power supply with an output voltage of 4.5 V, and the output terminal is connected to booster circuities 32 and 34. The booster circuitry 32 can supply a direct-current voltage of 5 to 12 V, and the output terminus is connected to a driver circuitry 36. The booster circuitry 34 is to supply a constant voltage of 5 V to a microcomputer 38.

The microcomputer 38 comprises an I/O interface 38*a* for communicating with external signals, ROM 38*b* for keeping computer programs, and RAM 38*c* for keeping data, and CPU 38*d* for processing operations. To the microcomputer 38 are installed a clock generating circuitry 40 for supplying 8 MHz clock signals to the microcomputer 38, and two oscillation circuities 42 and 44 for supplying a 5-50 Hz signal to control the displaying speed and for supplying a 0.2-2 kHz signal to control the scanning frequency, respectively.

The reference numeral 48 is a display panel that is mainly composed of the organic EL element of the present invention and is connected to the microcomputer 38 through the driver circuities 36 and 46. The driver circuitry 36 is for controlling the energization of the direct current voltage, supplied from the booster circuitry 32, to the display panel, and it comprises transistors connected separatory with the lines of electrodes in the vertical direction in the display panel 48. Thus, when either of the transistors in the driver circuitry 36 is actuated, the lines of electrodes in the vertical direction are energized with the voltage supplied from the booster circuitry 32. The driver circuitry 46 comprises transistors connected separatory to the lines of electrodes in the horizontal direction in the display panel 48. When either of the transistors in the driver circuitry 46 is actuated, the lines of electrodes in the horizontal direction connected to the transistors are grounded.

Since the information display in this example thus constructed, when the transistors in the driver circuities 36 and 46 are actuated in accordance with the instruction by the microcomputer 38, a prescribed voltage is supplied between the corresponding electrode lines in both the vertical and the horizontal directions in the display panel 48 to allow to emit the organic EL element positioned in the intersection point. Thus, for example, when a line of electrode in the horizontal direction is selected by appropriately controlling the driver circuitry 46 and then the selected line of electrode is grounded while the transistors, connected to the lines of electrodes in the vertical direction, are sequentially allowed to actuate by appropriately controlling the driver circuitry 36, the selected whole lines of electrodes in the horizontal direction are scanned in the horizontal direction to display the desired picture element. By sequentially repeating such a scanning in the vertical direction, a flame can be totally displayed. Since the driver circuitry 36 in this example has a data resistor for a line of electrode, transistors should preferably be actuated based on the data recorded in the data resistor.

The information to be displayed can be supplied externally by synchronizing with the display speed and cycle or, for example, information of specific patterns such as of characters can be previously recorded in the ROM38b and used as data. In the case of displaying television broadcasting by the NTSC method in general, the signals received are separated into horizontally- and vertically-synchronizing signals according to the horizontal and vertical frequencies based on the broadcasting standard, and the signals for images are converted into digital signals corresponding to the picture elements of the display panel 48. By appropriately synchronizing and supplying the digital signals to the microcomputer 38, the desired television broadcasting can be displayed on the display panel 48.

As described above, the present invention was made based on the establishment of novel 4-cyanocoumarin derivatives and the findings of their industrially-useful features. Since the derivatives exert a distinct sensitivity to visible light, they can be advantageously used as photosensitizes. For example, they can be applied for a variety of fields including the use for photopolymerization where photopolymeric compounds are irradiated, in the presence of or the absence of polymerization initiators, with visible light such as sun light, carbon arcs, high-pressure mercury lamps, xenon lamps, metal halide lamps, fluorescent lamps, tungsten lamps, argon-ion-lasers, krypton-ion-lasers, helium/cadmium lasers, helium/neon lasers, semiconductor lasers, second harmonic of YAG lasers, etc. Thus, the 4-cyanocoumarin derivatives of the present invention can be advantageously used in the fields, where the photosensitization by visible light is an essential technical factor, which include lithographic plates for printing such as in laser families, laser printers, color scanners, monotone scanners, photocompositions, planographic processes, gravure printing, flexographies, and silk-screen printing; and another fields of printing, publications, electronics, information recordings, chemicals, metals, automobiles, shipbuildings, and medical industries where inks, paints, chemical vapor depositions (CVD), photosensitive resins, photosensitive films, photosensitive coating agents, photo-restoring adhesives, resists for printing substrates, resists for integrated circuits, digital color proofs, holographies, substrates for optical recording disks, fillers for dental therapy, metal letterpress, metal plate finishing, die matrices, shadow masks for color televisions, etc.

Since the 4-cyanocoumarin derivatives of the present invention has a satisfactory color purity and a distinct fluorescent ability in a visible region, particularly, red-color region, they can be quite useful as luminescent agents in organic EL elements and laser-active substances in dye lasers, as well as luminous bodies as a lighting source for lighting devices in general, and information displays for displaying information visually.

The present invention, having these outstanding functions and features, is a significant invention that greatly contributes to this art.

While what are at present considered to be the preferred embodiments of the invention have been described, it will be understood that various modifications may be made therein, and the appended claims are intended to cover all such modifications as fall within the true spirits and scope of the invention.

What is claimed is:

1. A 4-cyanocoumarin compound represented by Formula 1:

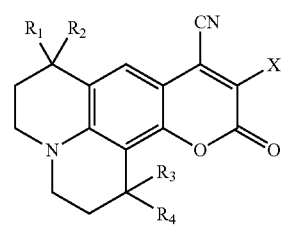

Formula 1 where in Formula 1, $R_1$ to $R_4$ are the same or different hydrogen atoms, alkyl groups, alkoxy groups, or aromatic hydrocarbon groups, wherein said aromatic hydrocarbon groups optionally have a substituent, with the proviso that $R_1$ to $R_4$ are neither (i) hydrogen atoms at the same time nor (ii) methyl groups at the same time; and X is a monovalent group selected from the group consisting of a hydrogen atom, cyano group, nitro group, carboxyl group, aryl group, alkyl group, and alkoxy group.

* * * * *